United States Patent [19]

Achter

[11] 4,066,361
[45] Jan. 3, 1978

[54] METHOD AND APPARATUS FOR DERIVING OXYGEN ASSOCIATION CURVES

[75] Inventor: Eugene K. Achter, Gaithersburg, Md.

[73] Assignee: Baxter Travenol Laboratories, Inc., Deerfield, Ill.

[21] Appl. No.: 668,548

[22] Filed: Mar. 19, 1976

Related U.S. Application Data

[63] Continuation of Ser. No. 504,112, Sept. 9, 1974, abandoned, which is a continuation-in-part of Ser. No. 446,089, May 1, 1974, abandoned.

[51] Int. Cl.$^2$ .................... G01N 33/16; G01N 21/16; G01N 21/22
[52] U.S. Cl. .................................... 356/41; 356/244; 356/205
[58] Field of Search ................ 356/41, 40, 39, 178, 356/186, 201, 205, 206, 244, 246; 23/230 B, 253 R

[56] References Cited

PUBLICATIONS

"A Gas-Hemogloben Diffusion Photometer," F. Kreuzer and L. Garceau, IRE Trans. on Medical Electronics, July, 1960, pp. 207-210.
"On the Accuracy of an Improved Method for the Measurement of O$_2$-Dissociation Curves . . . ," Banirdl et al., Physiology of Oxygen Transport to Tissue, Nov. 1973, pp. 325-331.
"Studies on the Function of Abnormal Hemoglobins . . . ," Kiyohiro Imai et al., Biochimica et Biophysica Acta 200, (1970), pp. 189-196.
"A New Method for the Rapid Determination of Oxygen Dissociation Curves . . . ," L. A. Kiesow et al., Clinica Chimica Acta 41, (1972), pp. 123-129.

Primary Examiner—Jon W. Henry
Attorney, Agent, or Firm—Henry W. Collins; Richard G. Kinney; Paul C. Flattery

[57] ABSTRACT

An apparatus and method for deriving an oxygen association curve for a blood sample wherein the sample is placed on a transparent support and is covered by a gas-permeable membrane element. The support is mounted in a gas treatment chamber with transparent windows on opposite sides of the support to provide an optical path through the support normal to the sample. Radiant energy is directed along this optical path, said radiant energy including two light frequencies, one having a wavelength at which there is substantially no change in absorbance as between oxygenated and deoxygenated blood and the other having a wavelength at which there is a relatively large change in absorbance as between oxygenated and deoxygenated blood. A controlled source of deoxygenating gas, such as nitrogen, and a controlled source of oxygen are connected to the chamber. An oxygen electrode is mounted in the chamber and generates the X component, corresponding to oxygen in the chamber, in an X-Y recorder. The difference in absorption of the two frequencies is measured and from this is derived a signal forming the Y component in the X-Y recorder, which thus provides a curve corresponding to the light absorbance changes in the sample while it is being oxygenated.

19 Claims, 10 Drawing Figures

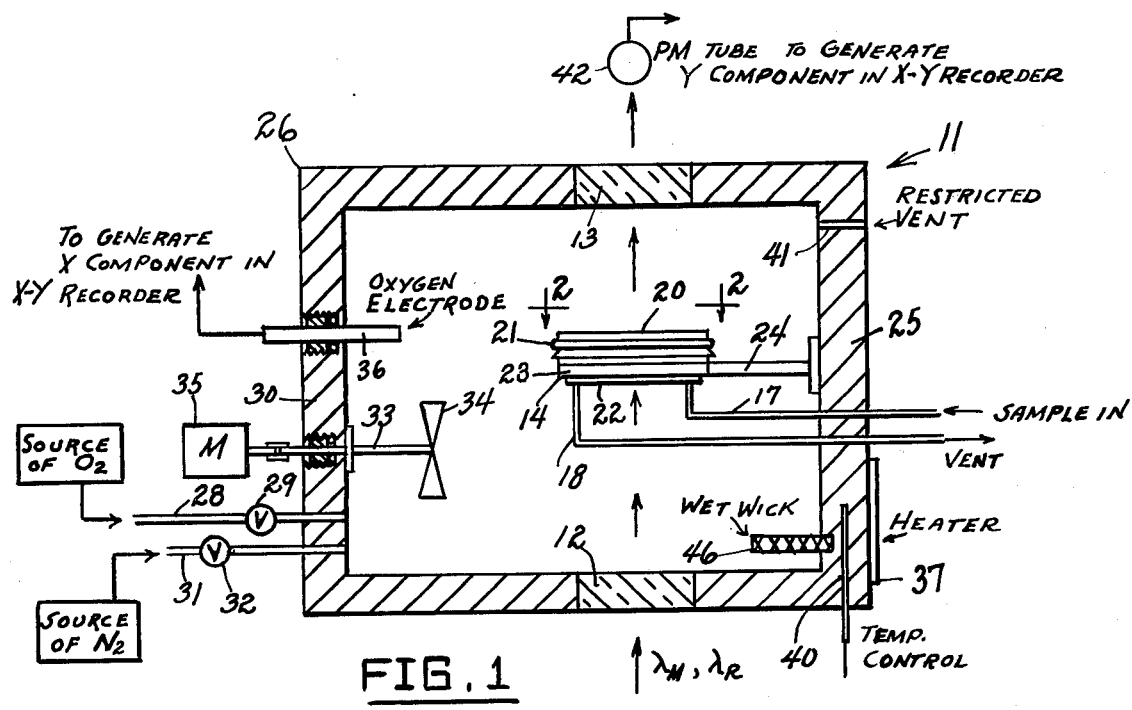
FIG. 1
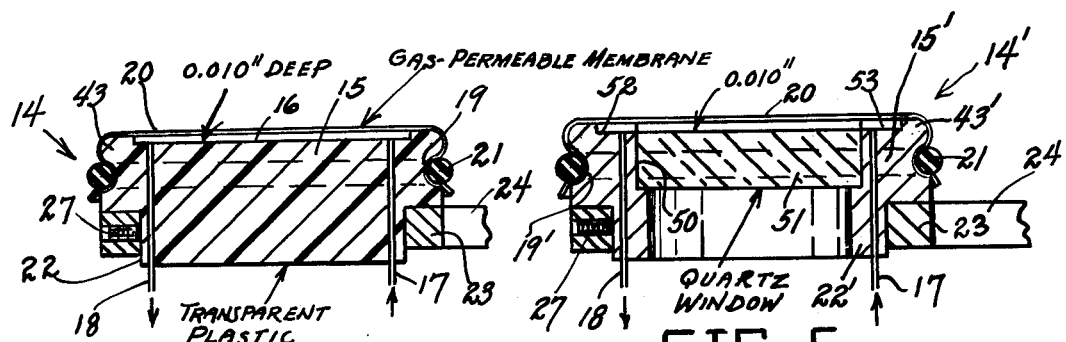
FIG. 3        FIG. 5
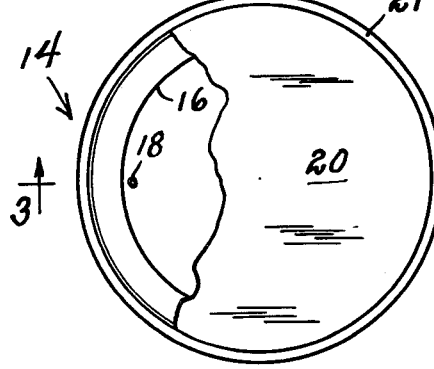   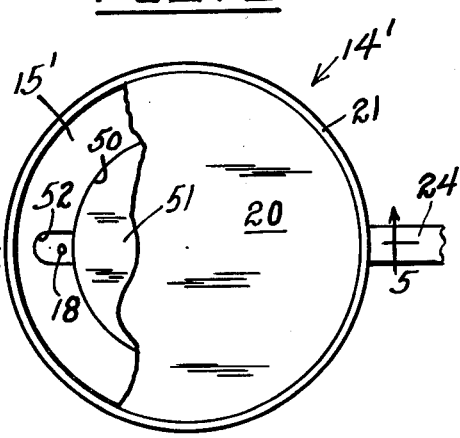
FIG. 2        FIG. 4

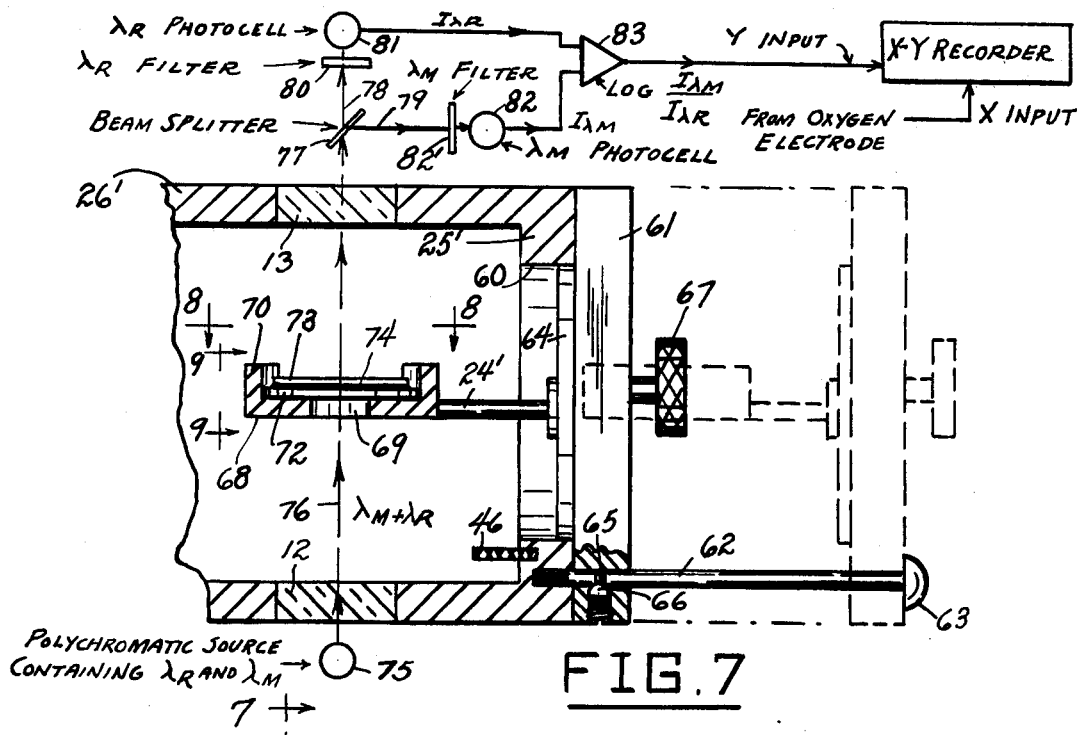
FIG.7
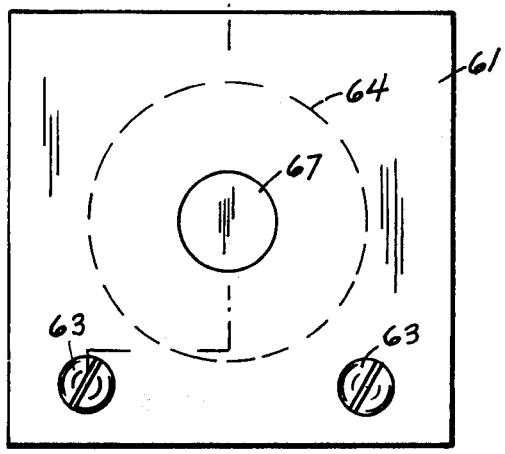
FIG.6
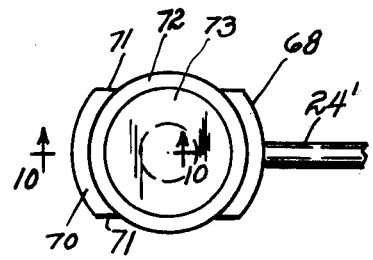
FIG.8
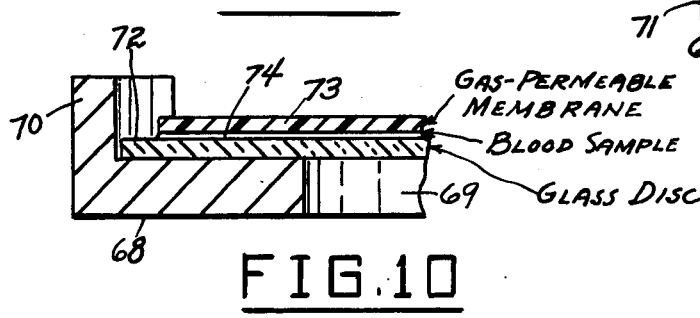
FIG.9
FIG.10

METHOD AND APPARATUS FOR DERIVING OXYGEN ASSOCIATION CURVES

CROSS REFERENCE TO RELATED APPLICATIONS

This application is a continuation of my earlier application Ser. No. 504,112, filed Dec. 9, 1974, now abandoned, which was a continuation-in-part of my still earlier application Ser. No. 446,089, filed May 1, 1974, also now abandoned.

This invention relates to methods and apparatus for measuring the oxygenation characteristics of blood or other material whose light-absorbing characteristics change while being treated with a reagent, and more particularly to a method and apparatus for deriving an oxygenation curve for a whole blood sample.

BACKGROUND OF THE INVENTION

The oxygen binding curve (commonly called the "oxygen dissociation curve") for hemoglobin is formed by the measurements of the fraction of total hemoglobin that is oxygenated as a function of the partial pressure of oxygen ($PO_2$) to which the hemoglobin sample is exposed. The entire curve and/or parameters derived from it are of substantial physiological and clinical significance. Currently used techniques in this field employ dual wavelength photometry, and such techniques comprise passing time-shared measure and reference beams $\lambda_M$ and $\lambda_M$ through the sample while it undergoes oxygenation and utilizing the differences in absorption of these beams as measured by a photomultiplier tube and associated circuitry for deriving the desired "oxygen dissociation curve", which is in fact an oxygen association curve.

SUMMARY OF THE INVENTION

The present invention encompasses a method and apparatus for deriving oxygen association curve information from a blood sample which includes arranging the sample in the form of a thin layer in a sample cell, subjecting the sample cell to a changing gaseous atmosphere that causes the sample to undergo the deoxy/oxy transition while both measuring the oxygen partial pressure in the cell and the change in absorbance of light by the sample.

The technique and apparatus of the present invention offer numerous advantages; among which are the following:

a. It permits use of undiluted whole blood, thereby avoiding possible nonphysiological artifacts.

b. It accomplishes deoxygenation of the blood sample without using harsh reagents, such as dithionate.

c. It requires only a very small sample volume, which is important in pediatric cases and for research or rare hemoglobins.

d. It provides a linear measure of fraction oxyhemoglobin over the complete range of oxygenation, unlike reflectance measurement techniques.

e. It generates continuous curves and provides for control and variation of $PO_2$ which is uncomplicated, reliable, and which requires only small quantities of compressed gases.

f. It employs an oxygen-sensing electrode which is inherently stable and has a long lifetime, and which is not in direct contact with the blood sample.

BRIEF DESCRIPTION OF THE DRAWINGS

Further advantages of the invention will be apparent from the following description and claims, and from the accompanying drawings, wherein like elements are identified by like indicia, and wherein:

FIG. 1 is a diagrammatic vertical cross-sectional view taken through a typical blood sample oxygenation association measurement assembly constructed in accordance with the present invention.

FIG. 2 is an enlarged fragmentary horizontal plan view of the sample cell employed in the assembly, said view being taken substantially on the line 2—2 of FIG. 1.

FIG. 3 is a vertical cross-sectional view taken subtantially on the line 3—3 of FIG. 2.

FIG. 4 is a fragmentary horizontal plan view similar to FIG. 2 but showing a modified form of sample cell according to the present invention.

FIG. 5 is a vertical cross-sectional view taken substantially on the line 5—5 of FIG. 4.

FIG. 6 is an end elevational view of another modified form of blood sample oxygen association measurement assembly in accordance with the present invention.

FIG. 7 is a vertical cross-sectional view taken substantially on the line 7—7 of FIG. 6 and diagrammatically showing associated optical and electrical components used with the assembly in this form of the invention.

FIG. 8 is a top plan view of the blood sample supporting member employed in the embodiment of FIGS. 6 and 7, said view being taken substantially on the line 8—8 of FIG. 7.

FIG. 9 is an elevational view of the sample supporting member taken substantially on the line 9—9 of FIG. 7.

FIG. 10 is an enlarged fragmentary vertical cross-sectional view taken substantially on the line 10—10 of FIG. 8.

DETAILED DESCRIPTION

The technique of the present invention involves the use of a sample cell wherein a thin film of blood is exposed to controlled $PO_2$ via a gas-permeable membrane, and through which simultaneously optical absorption spectroscopic measurements are performed. A film thickness of blood of 0.010 inch or less is employed to permit rapid oxygen exchange within the blood and to make the undiluted blood sample sufficiently transparent to permit the optical absorption measurements. The film thickness must be stable for stable optical measurements, and must not contain occluded bubbles, for both optical and gas exchange reasons.

Referring to the drawings, 11 generally designates an apparatus for deriving oxygen association curves in accordance with the present invention. The apparatus 11 comprises a gas chamber 26 of suitable opaque material, such as aluminum or the like, adapted to be mounted, for example, in the path of the time-shared monochromatic beams $\lambda_M$, $\lambda_R$ of a dual wavelength spectrophotometer. In the typical apparatus illustrated in FIG. 1 of the drawings, the chamber has a transparent window 12 in its bottom wall for admitting the time-shared beams $\lambda_M$, $\lambda_R$ and has another transparent window 13 in its top wall vertically aligned with window 12 to define an optical path therebetween, the emerging beams being directed toward the photomultiplier tube 42 of the spectrophotometer.

Designated generally at 14 is a blood sample cell which is horizontally mounted in the path of the time-shared monochromatic beams $\lambda_M$, $\lambda_R$. Referring to FIGS. 2 and 3, the cell 14 comprises a generally circular body 15 of suitable transparent material, such as transparent plastic material, concentrically formed in its top face portion with a shallow circular recess 16 having a depth of approximately 0.010 inch and a diameter of the order of ⅜ inch. Respective inlet and outlet capillary tubes 17 and 18 extend vertically and sealingly through diametrically opposite portions of the body 15 and communicate with corresponding diametrically opposite portions of recess 16. The body 15 is formed with a rounded-off rim portion 43 leading to a peripheral groove 19 which receives the marginal portion of a transparent gas-permeable membrane 20, said marginal portion being sealingly and clampingly secured in the groove 19 by a resilient O-ring 21, with the main portion of the membrane tightly stretched over the recess 16.

The gas-permeable transparent membrane 20 is about 0.001 inch thick and may comprise pure silicone rubber film, or suitable commercial transparent gas-permeable membrane, such as Perflex OM-110 silicone rubber copolymer, manufactured by Union Carbide Corp., Moorestown, New Jersey.

The body 15 is reduced at its lower portion, as shown at 22, and the reduced lower portion is supportingly received in a bracket ring 23 provided with a radial supporting arm 24 which is rigidly secured to the adjacent side wall 25 of chamber 26. Ring 23 is provided with a set screw 27 diametrically opposite arm 24 which clampingly secures the reduced lower portion 22 in the ring 23.

The capillary tubes 17 and 18 extend sealingly through side wall 25 of the gas chamber 26. An oxygen supply conduit 28 provided with a suitable control valve 29 extends sealingly through the opposite side wall 30 of chamber 26, and a nitrogen supply conduit 31 similarly provided with a suitable control valve 32 extends sealingly through said side wall 30. Rotatably and substantially sealingly supported in side wall 30 is the shaft 33 of a fan 34, suitably driven by an external electric motor 35. A conventional oxygen-sensing electrode 36 is sealingly mounted in wall 30 and extends into the chamber, the electrode being externally connected to suitable circuit means for generating the X component of a conventional X-Y recorder. The oxygen-sensing electrode 36 may be similar to Model 5331, manufactured by Yellow Springs Instrument Company, Yellow Springs, Ohio, of the type known as a "Clark Electrode".

A water-absorbent humdifying wick member 46, which can be readily moistened, is mounted in the lower portion of the chamber 26, for example in a recess provided therefor in the lower portion of wall 25. The wick 46 furnishes the required humidity to prevent the excessive drying out of the oxygen electrode 36 and blood sample. The chamber 26 is temperature controlled, to maintain a substantially constant temperature therein by means of an electric heater 37 secured to the chamber in heat-transmitting relation thereto, whose energization is controlled in a conventional manner by a temperature-sensing element 40 embedded in the chamber wall adjacent the heater.

The upper portion of wall 25 is provided with a restricted vent passage 41. In a typical embodiment, the wall thickness of the chamber was about 0.6 inch, and the vent passage 41 was about 0.025 inch in diameter.

In the associated dual wavelength spectrophotometer various wavelength pairs may be employed for the $\lambda_M$ and $\lambda_R$ monochromatic beams, for example, 650–800 nm, 547–560 nm or 650–724 nm. The advantages of employing a dual wavelength system of measurement include (a) automatic correction for any changes in scattered light during the generation of a test curve, (b) use of a reference beam path that also goes through the sample, and (c) the potential capability of measuring hematocrit and other parameters, as well as generating the oxygen association curve, at the same time.

A single wavelength measurement system may be employed with the gas chamber and blood cell apparatus of the present invention, providing reduced cost and greater simplicity of construction, but not providing automatic correction for possible changes in scattered light during the generation of the oxygen association curve.

In operation, the membrane cell 14 is supplied with a sample of whole blood, admitted therein through the inlet capillary tube 17. The oxy-deoxy transition is started in this environment, with the chamber 26 being first filled with $N_2$ (including about 5% $CO_2$) through conduit 31 by opening valve 32, whereby to deoxygenate the blood sample. The initial deoxygenation of the sample requires an exposure of about 15 minutes. Thereafter, with valve 32 closed and the spectrophotometer system in operation, an oxygen binding curve (oxygen association curve) is generated on the associated X-Y recorder by operating valve 29 to slowly introduce $O_2$ (including about 5% $CO_2$). The oxygen supply system may include a syringe pump or other pump to provide a rate of oxygen input sufficient to achieve 20% oxygen in the chamber in 5 to 10 minutes. The variation of $PO_2$ with time will be exponential rather than linear, so that the oxygen binding curve is preferably generated using the X-Y recorder, with the oxygen electrode 36 driving the X axis and the PM tube 42 providing the signals for generating the Y component in the recorder. Since the oxygen electrode 36 does not come in contact with the blood sample, the $PO_2$ in the chamber must be varied sufficiently slowly that the blood is always effectively in equilibrium with the $PO_2$ in the chamber.

The dimensions of fan 34 are chosen to provide uniform vigorous mixing during the test run.

The 0.010 inch blood layer in the cell 14 permits controlled oxygenation of the blood, as aboce described, within 5 to 10 minutes, with the initial deoxygenation requiring about 15 minutes. By employing a lesser blood layer thickness (for example, 0.004 inch or less) the required exposure times may be correspondingly reduced.

Mounting the cell 14 horizontally, as above described, eliminates possible difficulties associated with settling of red blood cells during long experiments.

The blood sample is pretreated with suitable reagent, such as Heparin, or other well known anti-coagulant, to prevent clotting. This is done at the time of drawing the blood from the patient.

FIGS. 4 and 5 show another form of membrane cell, designated generally at 14', in accordance with the present invention. The cell 14' comprises a stainless steel ring 15' formed with an annular internal seat 50 in which is cemented a circular quartz window 51 whose top face is approximately 0.010 inch below the top plane of the ring, to define the main blood sample-receiving recess. Diametrically opposite channel recesses 52 and 53 are formed in the top portion of the ring, communicating with said main recess. The capillary tubes 18 and 17 extend vertically and sealingly through the opposite portions of the ring and communicate with the channel recesses 52 and 53. The ring has the lower reduced portion 22' which is clampingly secured in the supporting ring 23 in the same manner as previously described in connection with FIGS. 2 and 3.

Ring 15' has the rounded-off top rim portion 43' leading to a peripheral groove 19', and a stretched transparent gas-permeable membrane 20 is secured over the blood sample recess by means of an O-ring 21 clamping the marginal portion of the membrane in the groove 19', as in the previously described cell 14.

Various means may be employed, other than by use of an O-ring, for securing the stretched transparent gas-permeable membrane over the blood sample recess. Thus, for example, the membrane may be clamped in a suitable jig assembly. A film of silicone rubber cement may be applied to the rim portion of the main cell body and this rim portion may be clamped against the membrane, stretching it taut, and held thereagainst until the cement is cured, after which excess membrane material may be cut away.

While the above-described procedure employs whole blood as a sample, it is also possible to employ diluted blood or hemoglobin solution as a sample in said procedure.

In some cases it is possible and desirable to omit the covering membrane 20 and merely employ a thin layer of blood of the order of 0.001 inch thick on a flat transparent supporting plate, suitably mounted in the chamber 26 in place of cell 14. Under these conditions, careful control of the humidity in the chamber is necessary.

In the embodiment illustrated in FIGS. 6 to 10, the gas chamber, shown at 26' is provided with a large circular aperture 60 in its right end wall 25', as viewed in FIG. 7. A vertical cover plate 61 is slidably supported on a pair of parallel horizontal, relatively long support rod members 62,62 threadedly secured respectively in the lower corner portions of end wall 25', said rod members being provided with outer head portions 63,63 to limit the rightward extension of cover plate 61 to the dotted view position thereof shown in FIG. 7. Cover plate 61 is formed with the integral inwardly projecting circular boss 64 shaped to substantially fit in the aperture 60 in the closed position of the cover plate. The support rod members 62,62 are provided at their inner end portions with annular detent grooves 65 and the bottom edge portion of cover plate 61 is provided with spring-biased detent balls 66 yieldably and lockingly engageable in the grooves 65 to hold the cover plate 61 in closed position, as shown in full-line view in FIG. 7. Cover plate 61 is provided externally with a central operating knob 67.

Rigidly secured to the central portion of boss 64 is the horizontal supporting arm 24' which carries the blood sample cell element shown at 68. The supporting cell element 68 comprises an originally annular opaque member having a bottom central aperture 69 and an upstanding peripheral flange 70, with opposite cutaway flats 71,71 as shown in FIG. 8 to provide finger access for removing samples, as will be presently described. As will be further described, the blood sample is supported on a circular transparent disc 72, of glass, or the like, placed in the seat defined by element 68, and is covered by a gas-permeable membrane disc 73 placed over the sample and held thereon by the surface tension of the blood sample, shown at 74 (see FIG. 10).

The dual wavelength optical system employed may be similar to that previously described, but a more economical system which may be employed comprises a suitable polychromatic light source 75 containing the reference wavelength $\lambda_R$ and the measure wavelength $\lambda_M$, arranged so as to provide a beam 76 directed upwardly through the bottom window 12, the aperture 69, the blood sample 74 between the discs 72 and 73, and through the top window 13. The beam 76, after absorption by the blood sample, passes through the top window 13 to a beam splitter 77, such as a half-silvered 45° mirror, and forms two respective exit beams 78 and 79, the beam 78 being transmitted through the half-silvered mirror and the beam 79 being reflected therefrom. Beam 78 passes through a suitable $\lambda_R$ filter 80 to a first phototube 81 and beam 79 passes through a suitable $\lambda_M$ filter 82' to a second phototube 82. The output currents $I_{\lambda R}$ and $I_{\lambda M}$ of the phototubes 81 and 82 are applied to the respective inputs of a conventional computing logarithmic amplifier 83, providing an output signal equal to log $I_{\lambda M}$ -log $I_{\lambda R}$, or log $I_{\lambda M}/I_{\lambda R}$.

The output signal of amplifier 83 is delivered to the Y input of the associated X-Y recorder. As in the previously described embodiments of the invention, an oxygen-sensing electrode is provided in the gas chamber 26' for generating the X component of the recorder.

In a typical arrangement according to FIGS. 7 to 10, the glass disc 72 has a diameter of approximately 18 mm. and the transparent membrane disc is about 10 mm. in diameter. The supporting cell element 68 is shaped to conformably receive the disc 72 in the manner shown in FIGS. 7 to 10, where it will be seen that portions of disc 72 project outwardly beyond the flats 71, 71 to enable them to be easily grasped between the operator's fingers when it is desired to lift the disc 72, carrying the blood sample 74 and the membrane disc 73, off the holder 68 (with the cover plate 61 in its open dotted view position of FIG. 7).

The sample blood layer to be tested is prepared as follows: a disc 72 is placed in the holder 68. A drop of blood of 1-2 microliters in volume is placed on the central portion of disc 72. The membrane disc 73 (which may be composed of General Electric MEM-213 material, manufactured by General Electric Co., Inc., Schenectady, N.Y., or equivalent) is placed over the blood sample, which then forms a thin layer 74 by capillary action combined with the weight of the disc. After this cover plate 61 is moved to its closed position, shown in full-line view in FIG. 7.

The blood layer 74 has a thickness of less than 25 microns, and may be as small as between 10 and 20 microns in thickness. This permits complete deoxygenation in 1.5 to 2.0 minutes, rapid one-step oxygenation in 3 to 5 seconds, and production of equilibrium oxygen association curves in about 5 minutes. By contrast, a blood layer 0.01 inch thick requires from 15 to 20 minutes for deoxygenation and 30 to 50 seconds for rapid one-step oxygenation. The use of the gas-permeable, non-porous membrane disc 73 also retards water loss and permits safe handling of the blood layer in ambient air.

The appropriate wavelengths for dual wavelength spectrophotometry where a blood layer of 25 microns or less in thickness is used are 438 and 448 nm, and therefore these wavelengths are preferably employed for $\lambda_M$ and $\lambda_R$.

With the sample installed in the holder 68 in the manner above described, it is first precycled for proper blood conditioning (a highly important requirement), as follows: the chamber 26' is rapidly flushed with nitrogen containing 5% $CO_2$, for example, for about one minute at a rate of 100 cc per minute, to deoxygenate the sample. The sample is then oxygenated rapidly by admitting oxygen containing 5% $CO_2$ for about 5 seconds at about 120 mm pressure. The X-Y recorder is then calibrated by adjusting it so that the optical signal provides a Y-component reading which is stored as representing 100% oxygenation. The chamber 26' is then purged with nitrogen containing 5% $CO_2$. After deoxygenation, the optical signal is again read and stored as 0% oxygenation. The two stored values are used to set the zero offset and scale expansion to the Y axis of the X-Y recorder so that the graph will automatically span 0–100% on the Y axis.

The oxygen association curve for the sample may then be derived by following the procedure previously described, namely, by admitting oxygen into the chamber and measuring the change in log $I_{\lambda M}/I_{\lambda R}$ against oxygen concentration, using the above-described optical system in cooperation with the X-Y recorder. This gives a measurement of the fractional change in optical density that corresponds to the fraction of oxyhemoglobin in the sample over the range of oxygen concentration in chamber 26'.

The technique herein described produces a blood layer that is relatively resistant to evaporation and quite stable with time, so that, for example, repeated association curve measurements can be made on the same sample.

As will be apparent, when a sample is to be removed from the chamber 26', the cover plate 61 is pulled open to its fully extended position, allowing the operator to easily remove the sample by grasping the projecting opposite edge portions of disc 72 between his fingers and lifting the disc out of the holder 68.

While certain specific embodiments of improved methods and apparatus for deriving oxygen association curves for blood samples have been disclosed in the foregoing description, it will be understood that various modifications within the spirit of the invention may occur to those skilled in the art. Therefore it is intended that no limitations be placed on the invention except as defined by the scope of the appended claims.

What is claimed is:

1. An assembly for use in a photometer for measuring oxygen association curves, comprising a chamber, means for transmitting a measuring light beam through the chamber, light-transmitting cell means in the chamber formed to support sample material in the chamber transverse to the optical path of the measuring light beam in the form of a thin flat layer, a source of deoxygenating gas, controlled conduit means connecting said deoxygenating gas source to said chamber, a source of oxygen, controlled conduit means connecting said oxygen source to said chamber, said cell means comprising a light-transmitting body and a gas-permeable light transmissive membrane placed on the body over the sample supported thereon, and oxygen-sensing means mounted in said chamber.

2. The assembly of claim 1, and wherein said oxygen-sensing means comprises an oxygen electrode.

3. An assembly for use in a photometer for measuring oxygen association curves, comprising a chamber, means for transmitting a measuring light beam through the chamber, light-transmitting cell means in the chamber formed to support sample material in the chamber transverse to the optical path of the measuring light beam in the form of a thin flat layer, a source of deoxygenating gas, controlled conduit means connecting said deoxygenating gas source to said chamber, a source of oxygen, controlled conduit means connecting said oxygen source to said chamber, said cell means comprising a light-transmitting body and a gas-permeable light transmissive membrane placed on the body over the sample supported thereon, and said chamber being provided with a restricted gas escape passage in a wall portion of the chamber.

4. An assembly for use in a photometer for measuring oxygen association curves, comprising a chamber, means for transmitting a measuring light beam through the chamber, light-transmitting cell means in the chamber formed to support sample material in the chamber transverse to the optical path of the measuring light beam in the form of a thin flat layer, a source of deoxygenating gas, controlled conduit means connecting said deoxygenating gas source to said chamber, a source of oxygen, controlled conduit means connecting said oxygen source to said chamber, said cell means comprising a light-transmitting body and a gas-permeable light transmissive membrane placed on the body over the sample supported thereon, and a light source forming said measuring light beam, said source containing at least two wavelengths, said wavelengths having different absorption characteristics when transmitted through a blood sample undergoing oxygenation, and means to compare the relative absorbances of said two wavelengths with the amount of oxygen admitted into the chamber.

5. The assembly of claim 4, and wherein the means to compare said relative absorbances with the amount of oxygen admitted into the chamber comprises means to derive a first electrical signal in accordance with said relative absorbances, means to derive a second electrical signal in accordance with the amount of oxygen admitted into the chamber, and means to plot said first signal against said second signal.

6. A sample cell assembly for measuring oxygen association curves of hemoglobin comprising a light-transmitting supporting body, transparent means on the body for supporting the blood sample in the form of a thin flat layer, a gas-permeable light transmissive membrane member mounted so as to overlie a blood sample on said and a ring-shaped supporting bracket member supportingly receiving and surrounding said reduced portion.

7. A method of deriving the oxygen association curve of a blood sample comprising arranging the sample in the form of a thin, flat layer, deoxygenating the sample by exposing it to a deoxygenating gas, then exposing the deoxygenated flat layer of blood sample to oxygen, continuously measuring the partial pressure of oxygen to which the same is exposed, passing radiation including two wavelengths through the sample while it is being oxygenated, one wavelength at which there is substantially no change in absorbance as between oxygenated and deoxygenated blood and the other wavelength at which there is a relatively large change in absorbance as between oxygenated and deoxygenated blood, and plotting a function of the relative absorbance for the two wavelengths against the partial pressure of oxygen as the sample is being oxygenated, wherein the thin flat layer is formed by placing the sample between a pair of light-transmissive members, at least one of which is gas-permeable, and allowing the sample to spread between the light-transmissive members by capillary action.

8. The method of claim 7, and wherein the flat layer of blood sample is first conditioned by exposure to a deoxygenating gas followed by exposure to an oxygenating gas.

9. An assembly for use in a photometer for measuring oxygen association curves, comprising a chamber, means for transmitting a measuring light beam through the chamber, light-transmitting cell means in the chamber formed to support sample material in the chamber transverse to the optical path of the measuring light beam in the form of a thin, flat layer, a source of deoxygenating gas, controlled conduit means connecting said deoxygenating gas source to said chamber, a source of oxygen, and controlled conduit means connecting said oxygen source to said chamber, wherein said cell means comprises a light-transmitting body, light transmissive supporting element mounted on said light-transmitting body and arranged to receive the sample material in the form of said thin, flat layer, and a light transmissive gas-permeable membrane member mounted so as to overlie the sample material.

10. The assembly of claim 9, and wherein said light-transmitting body is formed with seat means shaped to receive the light-transmissive supporting element.

11. The assembly of claim 10, and wherein the light transmissive supporting element projects from opposite sides of said seat means.

12. The assembly of claim 9, and wherein said chamber is provided with an extensible closure member slidably connected to the chamber and said light-transmitting body is supportingly connected to said extensible closure member.

13. The assembly of claim 12, and wherein said closure member comprises a vertical plate and wherein the chamber is provided with support rod means extending through and slidably supporting said plate for horizontal extension relative to the chamber.

14. A method of measuring the oxygen association curve of a blood sample comprising arranging the blood sample in the form of a thin, flat layer sufficiently thin to be substantially light transmissive and to permit rapid diffusion of oxygen throughout the thickness of the sample, first deoxygenating the sample by exposing it to a deoxygenating gas, then exposing the deoxygenated flat layer of blood sample to gaseous oxygen, measuring changes in light absorbance of said flat layer while it is being exposed to oxygen at known concentrations, and maintaining uniform distribution of the gaseous oxygen in the space to which the sample is exposed.

15. A method of deriving oxygen association curve information from a blood sample comprising arranging the sample in the form of a thin layer, causing the sample to undergo a transition between oxygenated and deoxygenated states by exposing the sample to a changing oxygen content atmosphere while measuring the partial pressure of oxygen of the atmosphere to which the sample is exposed, and while also measuring the light absorbance change characteristics of the sample.

16. Apparatus for deriving oxygen association curve information from a blood sample, comprising
a sample cell including means for receiving the blood sample in the form of a thin, flat layer; means for allowing the passage of light through the blood sample; and means for enclosing the sample in a gaseous atmosphere;
means for causing the gaseous atmosphere of the sample cell to be subject to a changing oxygen content so that the blood sample may be caused to undergo a transition between oxygenated and deoxygenated states;
means for measuring, directly, the oxygen partial pressure in the gaseous atmosphere of the sample cell;
means for measuring the change in absorbance of light directed through the blood sample in the cell by the sample; and
output means responsive to both of said measuring means for deriving and displaying the oxygen association curve information.

17. The apparatus of claim 16 wherein the means for measuring the oxygen partial pressure in the sample cell is a Clark electrode.

18. The apparatus of claim 16 wherein the cell includes means for stirring the atmosphere in the cell.

19. The apparatus of claim 16 wherein the blood sample is exposed to the cell atmosphere through a oxygen permeable silicone rubber copolymer membrane.

* * * * *

UNITED STATES PATENT OFFICE
CERTIFICATE OF CORRECTION

Patent No. 4,066,361　　　　　Dated January 3, 1978

Inventor(s) Eugene K. Achter

It is certified that error appears in the above-identified patent and that said Letters Patent are hereby corrected as shown below:

Column 8, line 49, before "and" insert -- blood supporting means, said body having a reduced portion, --.

Column 8, line 57, delete "same" and insert -- sample --.

Signed and Sealed this

Eleventh Day of July 1978

[SEAL]

Attest:

RUTH C. MASON
Attesting Officer

DONALD W. BANNER
Commissioner of Patents and Trademarks